(12) United States Patent
Aastrup et al.

(10) Patent No.: US 9,533,881 B2
(45) Date of Patent: Jan. 3, 2017

(54) SURFACE PREPARATION METHOD

(75) Inventors: Teodor Aastrup, Djursholm (SE); Daniel Wallinder, Solna (SE); Henrik Anderson, Järfälla (SE)

(73) Assignee: Attana AB, Stockholm (SE)

( * ) Notice: Subject to any disclaimer, the term of this patent is extended or adjusted under 35 U.S.C. 154(b) by 1638 days.

(21) Appl. No.: 11/666,194

(22) PCT Filed: Oct. 21, 2005

(86) PCT No.: PCT/EP2005/011357
§ 371 (c)(1),
(2), (4) Date: Apr. 24, 2007

(87) PCT Pub. No.: WO2006/045558
PCT Pub. Date: May 4, 2006

(65) Prior Publication Data
US 2009/0142789 A1    Jun. 4, 2009

(30) Foreign Application Priority Data
Oct. 25, 2004 (GB) .................................. 0423686.5

(51) Int. Cl.
| | |
|---|---|
| *C12Q 1/00* | (2006.01) |
| *B82Y 30/00* | (2011.01) |
| *B82Y 15/00* | (2011.01) |
| *C12Q 1/68* | (2006.01) |
| *G01N 29/02* | (2006.01) |
| *G01N 33/543* | (2006.01) |

(52) U.S. Cl.
CPC ............... *B82Y 30/00* (2013.01); *B82Y 15/00* (2013.01); *C12Q 1/6825* (2013.01); *G01N 29/022* (2013.01); *G01N 33/54353* (2013.01); *G01N 2291/0255* (2013.01); *G01N 2291/0256* (2013.01); *G01N 2291/0426* (2013.01)

(58) Field of Classification Search
CPC ....... B82Y 30/00; B82Y 15/00; G01N 29/022; G01N 33/5453; G01N 2291/0426; G01N 2291/0256; G01N 2291/0255; C12Q 1/6825
USPC ........................... 435/29; 422/82.01; 436/149
See application file for complete search history.

(56) References Cited

U.S. PATENT DOCUMENTS

| | | | |
|---|---|---|---|
| 5,658,732 A | 8/1997 | Ebersole et al. | |
| 6,203,981 B1 | 3/2001 | Ackley et al. | |
| 6,264,825 B1 * | 7/2001 | Blackburn et al. | 205/777.5 |
| 7,771,657 B2 * | 8/2010 | Mansson et al. | 422/82.01 |
| 2003/0153024 A1 | 8/2003 | Sullivan et al. | |
| 2004/0091602 A1 * | 5/2004 | Hwang et al. | 427/2.11 |

FOREIGN PATENT DOCUMENTS

| | | |
|---|---|---|
| DE | 10049901 | 5/2002 |
| EP | 0395222 | 10/1990 |
| WO | WO02055993 | 7/2002 |
| WO | WO2004057319 | 7/2004 |

OTHER PUBLICATIONS

Schlereth, Characterization of protein monolayers by surfact plasmon resonance combined with cyclic voltammety 'in situ', J. Electroanalytical Chem, 464:198-207, 1999.
Brusatori and Van Tassel, Biosensing under an applied voltage using optical waveguide lightmode spectroscopy, Biosensors Bioelectronics, 18:1269-1277, 2003.
Brett and Chiorcea, Effect of pH and the applied potential on the absorption of DNA on highly oriented pyrolytic graphite electrodes. Atomic force microscopy surface characterisation. Electrochemistry Communications, 5:178-183, 2003.
Ge et al, Electrioc potential control of DNA immobilization on gold electrode, Biosensors Bioelectronics, 18: 53-57, 2003.
Fixe et al. II, Immobilization and hybridization by single sub-millisecond electric field pulses, for pixel-addressed DNA microarrays, Biosensors Bioelectronics, 19:1591-1597, 2004.
Badia et al., Probing the electrochemical deposition and/or desorption of self-assembled electropolymerizible organic thin films by surface plasmon spectrosopy and atomic force microscopy, Sensors Actuators, 54:145-165, 1999.
Johnnson et al., Immobilization of proteins to a carboxymethyldextran-modified gold surface for biospecific interaction analysis in surface plasmon resonance sensors, Analytical Biochemistry, 198:268-277, 1991.
Kahn and Wernet, Adsorption of proteins on electro-conductive polymer films, Thin Solid Films, 300:265-271, 1997.
Llahiri et al., A strategy for generation of surfaces presenting ligands for studies of binding based on an active ester as a common reactive intermediate: A surface plasmon resonance study, Anal. Chem., 71:777-790, 1999.
Snowski et al., Rapid determination of single base mismatch mutations in DNA hybrids by direct electric field control, Proc. Natl. Acad. Sci. USA, 94:1119-1123, 1997.
Heaon et al., Electrostatic surface plasmon resonance: Direct electric field-induced hybridization and denaturation in monolayer nucleic acid films and label-free discrimination of base mismatches, Proc. Natl. Acad. Sci. USA, 96:3701-3704, 2001.
Fixe et al. I, Electric field pulse assisted pulse immobilization and hybridization of NA in the nanosecond time scale for genetic information and analysis , IEEE 12th Int. Conf. on Solid State Sensors, Actuators and Microsystems, Boston, MA, Jun. 8-12, 2003.
F. Fixe et al., "Electric Field Pulse Assisted Covalent Immobilization and Hybridization of DNA in the Nanosecond Time Scale for Genetic Information Analysis," The International Conference on Solid State Sensors, Actuators and Microsystems, Boston, Jun. 8-12, 2003.

* cited by examiner

Primary Examiner — Kara Johnson
(74) Attorney, Agent, or Firm — Banner & Witcoff, Ltd.

(57) ABSTRACT

A method of covalently immobilizing a charged chemical species on or near a sensor surface of a mass-sensitive chemical sensor, the sensor surface bearing functional groups capable of forming covalent bonds with the chemical species, the method involving the application of an electric field between the charged chemical species and the sensor surface such that the electrostatic attraction therebetween is increased.

28 Claims, 5 Drawing Sheets

SURFACE PREPARATION METHOD

FIELD OF THE INVENTION

This invention relates to a method for preparing a surface. In particular, though not exclusively, the invention concerns a method for enhancing the covalent immobilisation of charged molecular species on the sensor surface of a mass-sensitive chemical sensor, and an apparatus for carrying out such a method.

BACKGROUND OF THE INVENTION

Mass sensitive chemical sensing with a molecular recognition interface typically involves localisation or attachment of a first molecular species near or onto a sensor surface, which converts a subsequent localisation or binding interaction with a second molecular species into a readable signal. A mass sensitive chemical sensor can be defined as any device that allows for measurement of a property that scales proportionally to mass associated with or bound to a sensitive surface of that device. Several such sensor techniques can be utilised, such as evanescent wave-based sensors, e.g. surface plasmon resonance (SPR, which is capable of registering mass changes by the associated change in refractive index at the surface), optical waveguides (also dependent on refractive index changes associated with mass binding events), ellipsometry and acoustic wave devices (for example quartz crystal micro balances (QCMs)). These sensor approaches are well established in the art (see, for example, *Biomolecular Sensors*, Gizeli and Lowe. Taylor and Francis, London; 2002) and these types of instruments can be used for studies of chemical reactions in situ and for detection of certain molecules in a sample. Attachment of the first molecular species to the sensor surface can be performed by covalent coupling, adsorption or physical entrapment (e.g. in a polymer layer or by the use of a membrane). The covalent coupling can be done directly to the otherwise unmodified sensor transducer surface, to a polymer layer on the sensor surface or with the use of a chemical/biochemical "capture system". The best approach for a particular application depends on several factors including the nature of the sample, the sensor transducer type, the manner in which the sensor will be used and the surface chemistry.

For some applications, electrostatic repulsion between the first molecular species and the sensor surface may decrease the ability of a molecule to approach and become bound to the sensor surface. This effect can reduce the sensitivity and the number of possible immobilisation strategies. In the field of biosensing, covalent coupling of biomolecules via their superficial primary amino groups to a carboxylated sensor surface has been found to be a useful and versatile immobilisation strategy. This technology can be used for the determination of specificity, concentration, affinity constants, kinetic parameters, and monitoring of multimolecular interactions in various biomolecular systems. The immobilisation of proteins to a carboxymethyldextran-modified gold surface has been previously described (Johnsson et al. *Analytical biochemistry* 198, 266-277 (1991)). In the first step of the immobilisation procedure a mixture of NHS(N-hydroxy succinimide) and EDC(N-ethyl-N'-(dimethylaminopropyl) carbodiimide) is passed over a carboxymethyldextran gold sensor surface. The EDC/NHS injection activates the surface due to the transformation of a proportion of the carboxyl groups into reactive esters (N-hydroxy-succinimide esters). In general, not all of the carboxyl groups are activated, thus leaving a degree of negative charge in the sensor surface matrix. In the next step, a protein (as first molecular species) dissolved in a low-ionic strength buffer at a pH below the isoelectric point (pI) of the protein is passed over the activated surface. The protein is concentrated in the matrix by electrostatic attraction between the positively charged protein and the negatively charged carboxyl groups in the matrix. During this process the NHS-esters react with the primary amino groups of the protein. The electrostatic adsorption uptake and thus also the covalent immobilisation will decrease with the buffer ionic strength. This is due to competition between the positive proteins and other positive ions in the solution. Therefore a low-ionic strength buffer is preferably used. In the last step, the remaining NHS-esters are transformed into amides by injection of ethanolamine hydrochloride. This step also removes electrostatically (i.e. non-covalently) bound material, although a subsequent optional injection of buffer or dilute acid can be employed to enhance this process. A key parameter in the covalent immobilisation is the pH of the protein solution. The covalent binding of the proteins to the active esters is favoured by a high pH (when the primary amino groups of the protein are uncharged). On the other hand, pH must be lower than the isoelectric point of the protein to achieve the electrostatic attraction of the protein to the negative carboxyl groups in the sensor surface matrix. It has generally been found that a successful immobilisation can only be performed at a pH lower than the isoelectric point of the protein, i.e. when the protein is positively charged. At the low pH value needed for relatively acidic proteins, however, both the protein binding capacity of the matrix and the reactivity of the protein is low. This immobilisation procedure has, until now, therefore been limited to proteins with pI higher than 4.

Brett et al. (*Electrochem. Comm.* 5, 178-183 (2003)) have described the adsorption of DNA onto pyrolytic graphite in the preparation of an electrochemical biosensor. Application of an electric potential during adsorption led to a stronger DNA-electrode surface interaction and improved DNA films were obtained in a lower pH buffer, i.e. when the charge on the DNA can be expected to be reduced. Badia et al. (*Sensors and Actuators B* 54, 145-165 (1999)) disclose a surface plasmon spectroscopy/atomic force microscopy study of alkanethiol deposition and desorption on gold surfaces under electric potential control. Similarly, Brusatori and van Tessel (*Biosensors and Bioelectronics* 18, 1269-1277 (203)) employed optical waveguide light mode spectroscopy to monitor electric potential-controlled adsorption of proteins on an indium tin oxide film. Potential dependent protein adsorption has also been monitored using SPR by Schlereth (*J. Electroanal. Chem.* 464, 198-207 (1991)).

Heaton et al. (*PNAS USA* 98, 3701-3704 (2001)) have examined the hybridisation and denaturation of DNA duplexes under an applied electrostatic field using SPR. Similar experiments are reported in U.S. Pat. No. 6,203,981. In DE10049901, adjacent and independently chargeable 'mobilisation' electrodes and detection electrodes are used to concentrate charged analytes for detection. The applied electric field accelerates and facilitates detection (e.g. by impedance changes). The electric field-augmented binding event concerned, however, is non-covalent (e.g. DNA hybridisation), with no consideration given to the additional problems involved in achieving covalent attachment of chemical species. Ge et al. (*Biosensors and Bioelectronics* 18, 53-58 (2003)) have described the effect of applied potential on the covalent immobilisation of DNA on a gold surface modified with a layer of aminoethanethiol (AET) for the purpose of constructing molecular logic circuits. Such an approach is not, however, appropriate for the preparation of a sensor surface for a mass-sensitive chemical sensor—the AET layer, with its short alkyl claims, would not provide a sufficiently ordered surface for mass-sensitive chemical sensing, and non-specific binding would consequently be high. In addition, the amino-groups on the surface will make the surface highly positive, which will further increase non-specific binding effects in many applications since most proteins have a net negative charge at physiological pH. Furthermore, the effects reported using this chemical coupling scheme are likely to be at least partially due to non-covalent attachment to the surface.

In EP0395222, an SPR study is conducted on the non-covalent capture and release of polarisable species under the influence of an alternating electric potential. U.S. Pat. No. 5,858,799 describes an electrochemical study during which an applied potential is used to oxidise and/or reduce analytes at the surface of an SPR metal film.

Thus, the prior art primarily deals with the effect of applied electric field on the adsorption or other non-covalent immobilisation of chemical species at a surface. No consideration is given to the particular difficulties which are presented when covalent immobilisation is required in an ordered and controllable manner at or near a sensor surface of a mass-sensitive chemical sensor. Those methods which are concerned with covalent immobilisation are either limited to molecular species having particular charge characteristics or do not allow the control of immobilisation and surface characteristics required for chemical sensing applications.

SUMMARY OF THE INVENTION

It is therefore an object of the present invention to provide a method which addresses the problems identified in relation to the above prior art.

Accordingly, one aspect of the present invention provides a method of covalently immobilising a charged chemical species on or near a sensor surface of a mass-sensitive chemical sensor, the sensor surface bearing functional groups capable of forming covalent bonds with the chemical species, the method involving the application of an electric field between the charged chemical species and the sensor surface such that the electrostatic attraction therebetween is increased.

The method of the present invention allows the repulsive electrostatic interaction between charged chemical species and sensor surfaces bearing the same charge as the chemical species to be at least partially overcome. This results in an increase in the amount of charged chemical species coming into the required proximity with the functional groups of the sensor for covalent reaction therebetween to take place. Since, in many applications, covalent immobilisation efficiency is dependent both on characteristics of the charged chemical species and the prevailing conditions of the dispersion (e.g. solution or suspension, or gaseous phase; in most embodiments of the invention, the charged chemical species will be present in solution) containing the charged chemical species (e.g. pH, ionic strength, temperature), the method of the invention allows a far wider range of chemical species to be covalently immobilised for chemical sensor analysis and under a greater range of conditions.

The term 'charged chemical species' is intended to include both chemical species containing groups which are permanently charged and chemical species whose charge is influenced by the pH of the dispersion. In the latter type of chemical species, it is possible under certain pH conditions (e.g. when the pH is at the pI of a protein) for the chemical species to bear a net charge of approximately zero. In such a case, an appropriate pH of the dispersion can be chosen to give the chemical species a positive or negative net charge; the direction of the electric field would then be chosen based on the net charge of the chemical species (or vice versa). In some embodiments of the method of the invention, therefore, an additional step is employed of adjusting the pH of the dispersion to alter the charge on the chemical species so as to enhance its attraction to the sensor surface.

The method also allows an improvement in the efficiency of covalent immobilisation of charged chemical species at or near a sensor surface bearing the opposite charge to the chemical species. In this case, the existing electrostatic attraction between chemical species and surface is augmented by the applied electric field.

In certain embodiments, the sensor surface bears a net negative charge. In such embodiments, the sensor surface preferably bears a plurality of carboxyl groups. Preferably, a proportion (which may be up to 100%) of the functional groups (e.g. carboxyl groups) are activated.

Such an immobilisation strategy, with carboxyl activation using, for example, EDC/NHS, provides an efficient covalent binding of amino-bearing (or other similarly reactive group-bearing) chemical species to the sensor surface. The approach provided by the present invention allows the efficient covalent immobilisation of such species to a sensor surface essentially regardless of the net charges on the chemical species and the surface.

In certain embodiments of the present method, the charged chemical species has a net negative charge during the immobilisation. Under these conditions, more of the groups of the chemical species which are involved in covalent binding to the sensor surface will be available for such a reaction. The efficiency of covalent immobilisation can be modified simply by altering the applied electric potential. Accordingly, if a particularly acidic protein, for example, is used as the charged chemical species for binding to a net negatively charged or neutral surface, efficient immobilisation can still be achieved even at the higher pH conditions generally required to enable the covalent coupling reaction to proceed, simply by application of a suitably high positive potential in the region of the sensor surface. In other embodiments, a chemical species with a net positive charge (e.g. a cationic protein or polyamine) may be used. In such a case, the electric field may be used to attenuate the repulsion between the chemical species and a net positively charged surface, or to increase the attraction between the chemical species and a net negatively charged or essentially neutral surface.

In another embodiment of the invention, the method can be used to immobilise charged chemical species on an essentially neutral surface bearing functional groups, preferably activated functional groups. The efficiency of immobilisation to a neutral surface would normally be low since the conventional methods to achieve electrostatic attraction of charged chemical species to an activated surface would be ineffective. The method provides means to efficiently immobilise charged chemical species onto neutral surfaces by applying an electric field between the sensor surface and the dispersion of charged chemical species. Having a neutral biosensor surface is often desirable since it will give rise to minimal electrostatically-induced non-specific binding effects, thereby increasing the practical sensitivity of the biosensor. A suitable surface could be a surface that contains functional groups, e.g. carboxyl groups, at a reduced surface density (the density of the functional groups being reduced by interspersion of the molecules bearing the functional groups among molecules bearing neutral and non-activated groups, such as hydroxyl or alkoxy (e.g. methoxy or ethoxy) groups, for example, instead of functional groups), so that each of the carboxyl groups can first be activated rendering an essentially, preferably completely, neutral surface. In the second step a dispersion of charged chemical species is introduced and an electric field is applied to attract the species to the surface. The species becomes covalently bound to the activated groups of the surface and remaining activated groups are deactivated with an agent that produces a neutral product. A neutral sensor surface is achieved, carrying only the charge introduced by the charged chemical species. A surface containing functional groups interspersed among neutral and non-activated groups also has the advantage that the distribution of charged chemical species on such a surface following the covalent binding step is more disperse. This tends to make the charged chemical species behave more like it would in dilute solution and hence improves both its affinity and native binding characteristics when a potentially interactive partner molecule is introduced to the surface for analysis of binding.

In preferred embodiments of the method, the net charge on the charged chemical species is pH-dependent. The charged chemical species is preferably a macromolecule or a microorganism or cell. Preferred macromolecules include polypeptides (including enzymes and receptors), polynucleotides and polysaccharides.

In embodiments of the method in which a polypeptide is the charged chemical species, the polypeptide may have an isoelectric point of approximately 4 or less. As mentioned above, the covalent immobilisation strategies employed hitherto have been limited in their application to polypeptides having a pI higher than 4. The present method thus greatly extends the range of charged chemical species which can be usefully immobilised to a sensor surface for chemical sensing techniques.

It is preferred that the sensor surface used in the method of the invention comprises a tridimensional porous matrix, the functional groups of the sensor surface being distributed in three dimensions within the matrix. Such an arrangement allows an increase in the surface area of the sensor surface. This allows a higher loading of the charged chemical species on the sensor surface and thus an improved sensitivity of the method. The porous matrix may comprise a hydrogel. The porous matrix is preferably formed from a biocompatible polymeric material, such as a polysaccharide material, e.g. carboxymethyldextran.

In certain embodiments of the present method, the electric field is applied by means of working and counter electrodes in electrical contact with a dispersion of the charged chemical species introduced into the vicinity of the sensor surface, one of the working or counter electrodes being formed by a metallic component of the sensor surface. Such an arrangement is relatively straightforward to assemble and may be employed in a controllable manner under a wide variety of conditions of ionic strength of the dispersion of the charged chemical species. The term 'electrical contact' as used herein implies physical contact between the electrodes and the dispersion, or contact via an interposed conducting material, such that current may flow between the electrodes via the dispersion. It is preferred that, in such arrangements, a reference electrode is directly or indirectly electrically connected to the dispersion and the working and counter electrodes. The reference electrode may be a standard electrochemical reference electrode (such as a saturated calomel electrode (SCE), or an electrode based on Ag/AgCl or Hg/HgO). The use of a three electrode approach allows better control of the potential of the working electrode. The reference electrode may be indirectly connected to the dispersion of charged chemical species and the other electrodes via a salt-bridge. The three electrode approach also allows the possibility of controlling redox reactions at or near the sensor surface, thus further extending the range of possible immobilisation strategies which may be employed in carrying out methods according to the invention.

Alternatively, in some embodiments of the invention, the electric field is applied by means of working and counter electrodes, at least one of which is substantially electrically insulated from a dispersion of the charged chemical species introduced into the vicinity of the sensor surface. The advantage of such embodiments is that, since at least one of the electrodes is substantially electrically insulated from the dispersion of the charged chemical species, no (or only minimal) current will flow between the working and counter electrodes. This reduces the possibility of unwanted redox reactions in the dispersion and the possibility of gas evolution (such as $H_2$ or $O_2$) from such processes. The term 'substantially electrically insulated from' as used herein implies that the electrode concerned is not in physical contact with the dispersion of chemical species, nor in electrical contact by means of an interposed conducting material. Under these circumstances, current flow between the electrodes, via the dispersion, is minimised.

In many instances, one of the working or counter electrodes is formed by a metallic component of the sensor surface. The metallic component of the sensor surface may be in electrical contact with the dispersion of the charged chemical species. The metallic component may, however, be at least partially covered with a layer of low electrical conductivity material. Such a material may comprise a polymer or a self-assembled monolayer.

The metallic component of the sensor surface may, for example, be the noble metal film (e.g. Ag or Au) of a SPR chemical sensor, or the AC driving electrode of a QCM which is exposed, in use, to the dispersion of chemical species.

In embodiments in which at least one of the working and counter electrodes is substantially electrically insulated from the dispersion, one or both of these electrodes may be located adjacent the sensor surface and may be substantially electrically insulated therefrom so as to allow the application of an electric field substantially transverse to the sensor surface.

In a typical operating orientation, one electrode may be located beneath the sensor surface, with the other electrode located above the sensor surface and in contact with the dispersion of charged chemical species. Equally, when one of the working or counter electrodes is formed by a metallic component of the sensor surface, the other electrode is located beyond (e.g. above) the dispersion of chemical species and is substantially electrically insulated therefrom.

In particular embodiments, the chemical sensor may be formed from material of low electrical conductivity. In such embodiments, one of the working or counter electrodes is located directly adjacent (e.g. beneath) the sensor surface, with the other electrode being located in contact with the dispersion or beyond (e.g. above) the dispersion and substantially electrically insulated therefrom. Thus, the method of the present invention allows electric field-assisted covalent immobilisation of charged chemical species in embodiments wherein both the working and counter electrodes are substantially electrically insulted from the dispersion of the charged chemical species. This has the advantage that neither of the electrodes comes into contact with the dispersion of charged chemical species and thus the likelihood of corrosion or contamination is reduced, therefore increasing the reusability of the chemical sensor and electrodes from one sample of chemical species to another.

For best results when one or both of the working or counter electrodes is substantially electrically insulated from the dispersion of charged chemical species, it is preferred to use a dispersion having a low ionic strength, preferably below 100 mM and more preferably below 10 mM with respect to low molecular weight ions. Depending on the application, it may be preferred to use an even lower ionic strength, e.g. 5 mM or below, or deionised (e.g. ultrapure) water. However, the method is highly adaptable, and other parameters can be modified to compensate for changes in ionic strength, e.g. changing the pH or changing the applied potential.

In preferred embodiments of the method of the invention, the chemical sensor resides within, or forms part of, a flow cell for ingress and egress of the dispersion of the charged chemical species to and from the vicinity of the sensor surface. Such an arrangement provides ready access to the sensor surface, which is convenient for most charged chemical species and types of sensor surface and allows enhanced control over the rate of introduction and removal of chemical species from the chemical sensor. In those embodiments where the chemical sensor forms part of a flow cell, the chemical sensor is typically engaged, in use, with a component having a recess and means for the ingress and egress of fluid samples to and from that recess. The recess, in cooperation with the sensor surface of the chemical sensor, forms a cell which is closed apart from the means for ingress and egress of fluid.

In preferred embodiments of the method of the invention, the chemical sensor is a piezoelectric sensor (for instance a quartz crystal microbalance), an evanescent wave-based sensor such as a surface plasmon resonance-based chemical sensor, or an optical waveguide-based chemical sensor.

In carrying out the method of the invention, it can be advantageous to have an additional step, subsequent to the covalent immobilisation step, in which the applied electric field is reversed. This additional step may be useful for removing non-covalently bound charged chemical species from the chemical sensor before the sensor is used in analyses. This step may be combined with an adjustment of the pH of the dispersion in the vicinity of the sensor surface, so as to alter the net charge on a pH-influenced charged chemical species and thereby increase the repulsion between the charged chemical species and the sensor surface under the reversed-field conditions.

In another aspect of the present invention, there is provided an apparatus comprising a mass-sensitive chemical sensor having a sensor surface bearing functional groups capable of forming covalent bonds with a charged chemical species introduced, in use, into the vicinity thereof, and means for applying an electric field between the charged chemical species and the sensor surface so as to increase the electrostatic attraction therebetween. Such an apparatus may be used for carrying out the method described above and may have one or more of the optional/preferred features described above in relation to that method.

In preferred apparatus of the invention, the chemical sensor resides within, or forms part of, a flow cell for ingress and egress of a dispersion of the charged chemical species to and from the vicinity of the sensor surface.

It is preferred, for carrying out certain analyses, that the means for applying an electric field comprises working and counter electrodes, at least one of which does not, in use, come into physical contact with a dispersion of the charged chemical species introduced into the vicinity of the sensor surface. The advantages and applications of such an apparatus are discussed above.

In a related aspect, the present invention also provides apparatus comprising a mass-sensitive chemical sensor based on an evanescent wave device such as a surface plasmon resonance sensor or on a piezoelectric device such as a quartz crystal microbalance and having means for applying an electric field between the sensor surface of the chemical sensor and a charged chemical species introduced, in use, into the vicinity of the sensor surface so as to increase the electrostatic attraction therebetween. Such an apparatus is capable of highly sensitive and specific analyses of molecular interactions in real time, without the limitations imposed by repulsive electrostatic forces between the charged chemical species and the sensor surface which are often set up in useful covalent immobilisation strategies. The apparatus also exhibits improved covalent immobilisation efficiency under circumstances where the charged chemical species and the sensor surface bear opposite net charges.

The invention also provides, in a further aspect, the use of an applied electric field to assist covalent attachment of a charged chemical species to a sensor surface of a mass sensitive chemical sensor, wherein the sensor surface bears functional groups capable of forming covalent bonds with the charged chemical species. The advantages of using an applied electric field in conjunction with a mass sensitive chemical sensor are discussed above.

In a related aspect, the invention also provides the use of an applied electric field to control the binding orientation of a charged chemical species to a sensor surface of a mass sensitive chemical sensor. The preferred features of the methods described above may also be usefully deployed in such a use.

The invention will now be described in more detail by way of example only and with reference to the appended drawings, of which

DETAILED DESCRIPTION OF THE INVENTION

Example 1

Chemical Sensor Apparatus

By applying a positive potential at the gold surface of a biosensor comprising a gold film modified with a carboxylated polymer layer, it is possible to overcome the repulsive effect between negatively charged proteins and the negatively charged carboxyl groups, whereby a covalent coupling strategy such as the amino coupling immobilisation procedure described above can also be used for proteins with a pI lower than 4. The purpose of the applied electric field is to increase the transport of proteins to the polymer matrix of the sensor surface so that they are able to react with the N-hydroxysuccinimide esters. The electric field can be applied by a variety of different techniques over a mass sensitive sensor such as a QCM or a SPR-based sensor. Two such techniques for applying the electric field are as follows.

In the first technique, the electrodes are in contact with the sample and buffer solutions. Preferably, a three electrode set up is used. By using a three electrode electrochemical cell with the sensor as working electrode, a polarisable and chemically stable electrode such as platinum as counter electrode, and a standard reference electrode (such as SCE, Ag/AgCl or Hg/HgO), the potential of the sensor/working electrode can be better controlled compared to a two electrode system. The reference electrode can be electrically connected to the sample and the other electrodes in a flow cell via a salt-bridge. A potentiostat/galvanostat is preferably used to control the system. Besides controlling the potential of the working electrode/sensor it is possible to use certain redox reactions to change the chemical affinity between the molecule to be covalently immobilised and the sensor surface. It is also possible to change the pH near the electrode, which may influence the number of possibilities for the molecule to attach to the sensor surface. The advantage of using this technique is that the electric field can be very carefully regulated even if the sample and buffer solutions are highly conductive. In addition, the three electrode setup can be used to control redox reactions on the surface which could increase the number of available immobilisation methods using the surface.

However, the three electrode setup where the electrodes are in contact with the solution has some disadvantages under some analytical conditions: (i) the conductive surfaces may be incompatible with the biological samples; (ii) contamination from the reference- and counter electrode may distort analysis or at least require extensive rinsing between measurements which may be unpractical when the electrodes are mounted in the measuring system; (iii) Faradic currents may induce unwanted redox reactions which can change the chemistry of the sample and even cause gas evolution. The induced current can also change the pH in the vicinity of the electrodes. At the cathodic electrode the reduction of oxygen or the evolution of hydrogen will increase the pH, while the hydrolysis of metal ions at the anode can decrease the pH.

Figure 3:
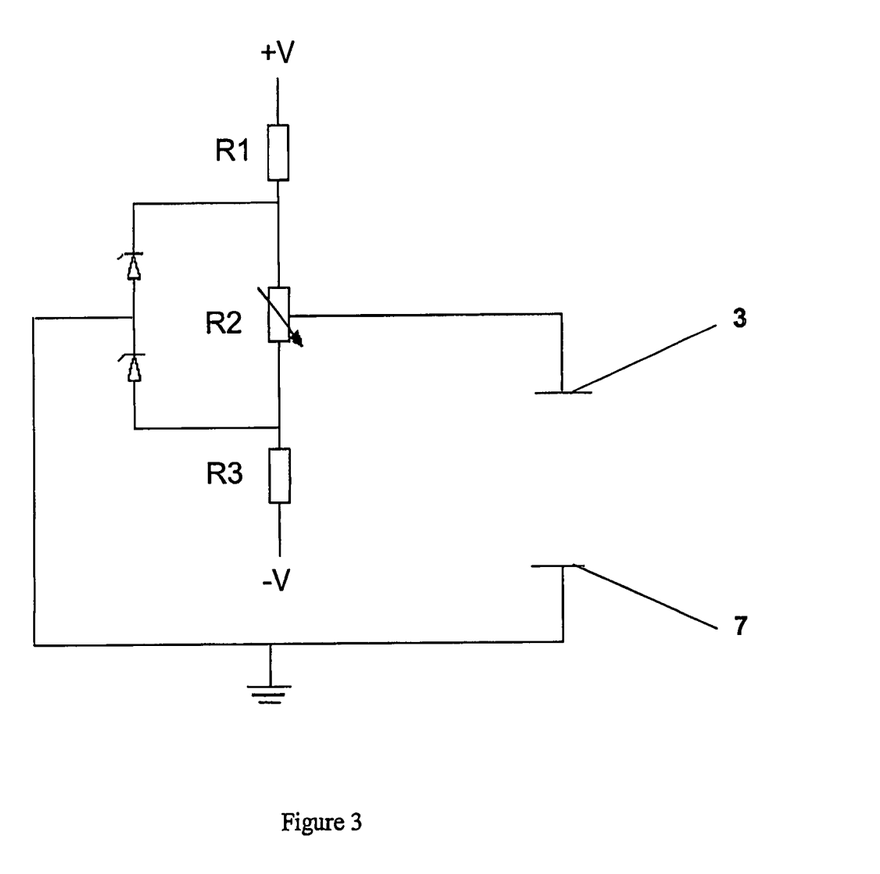
FIG. 3 shows an electrical schematic for applying and controlling a potential between two electrodes.

To resolve these issues an alternative electrode configuration may be used. One of the electrodes is placed electrically insulated from the sample and a second electrode is the sensor surface or is located in close proximity (e.g. directly beneath, in an operating orientation where the sample is introduced above the sensor surface) to the sensor surface. The sensor surface can be in electrical contact with the sample or alternatively covered with an electrically low conductive layer. The low conductive layer can be a polymer or a self-assembled monolayer (SAM). An example of a SAM is thiol-containing long alkyl chains (preferably $(CH_2)_{10}$ or longer) on gold. If the sensor is not made of an electrically conducting material the second electrode can be placed directly beneath the sensor device. The sample should usually be diluted in a buffer with low ionic strength, since the electric field could be screened somewhat if a high ionic strength buffer were used, thereby limiting the electric field strength that the sample molecules would be exposed to. The shape and distance between the electrodes depends on the desired electrical field over the sensor surface and constraints from the measuring device associated with the chemical sensor. The distance between the electrodes can typically be varied up to several centimetres. The sample can be flowing over the sensor in the liquid or vapour phase or can be stationary. One example of possible geometry is presented in FIG. 1 where the sample liquid is flowing over the sensor. The flow cell element (1) and fluid channels (2), are preferably formed from substantially non-conducting materials. A voltage source (8) is connected to the metal counter electrode (3) and the sensor element (7), whereby a potential can be applied therebetween. The electric field strength can be controlled by setting the potential between the electrodes (3) and (7). The potential can be applied using the simple circuit shown in FIG. 3 or by any other another suitable device capable of maintaining a relatively stable potential. Since at least one of the electrodes is not in direct electrical contact with the liquid sample, no current will flow between the electrodes. Thus, unwanted redox reactions and the possibility of gas evolution (such as hydrogen or oxygen gas) can be avoided. The created setup can be used to utilise electrostatic attraction or repulsion to attract target molecules to the sensor surface in order to increase the possibility of covalent attachment of those molecules to the sensor or to reduce non-specific binding to the sensor surface.

The electrode arrangement of the present invention may usefully be mounted on a flow cell with a sensor which is a component of an analytical apparatus. The apparatus is intended for sensing of chemicals and chemical reactions in liquids. On attachment of molecules to the sensor surface, the sensor provides a signal which is proportional to the mass of attached molecules.

Figure 1:
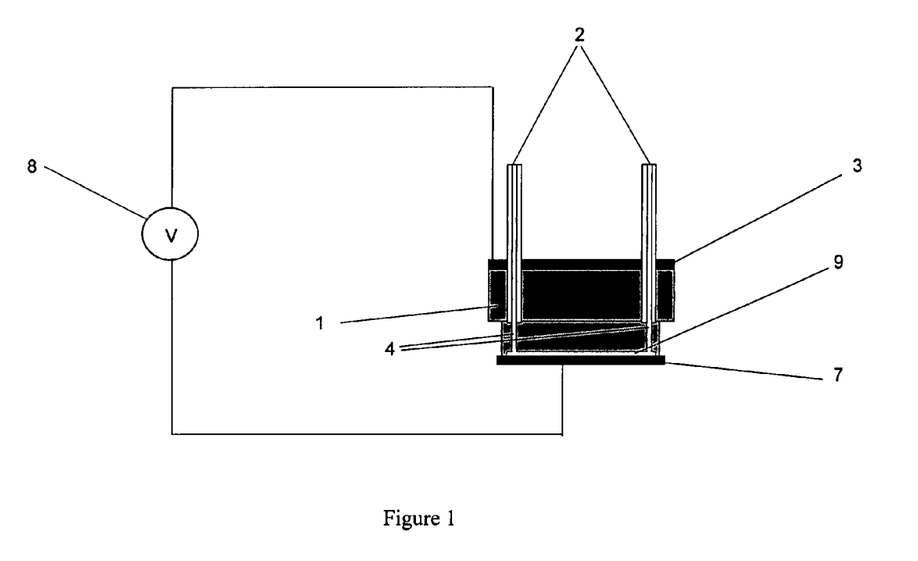
FIG. 1 shows a cross-sectional schematic view of a flow cell and counter electrode.
Figure 2:
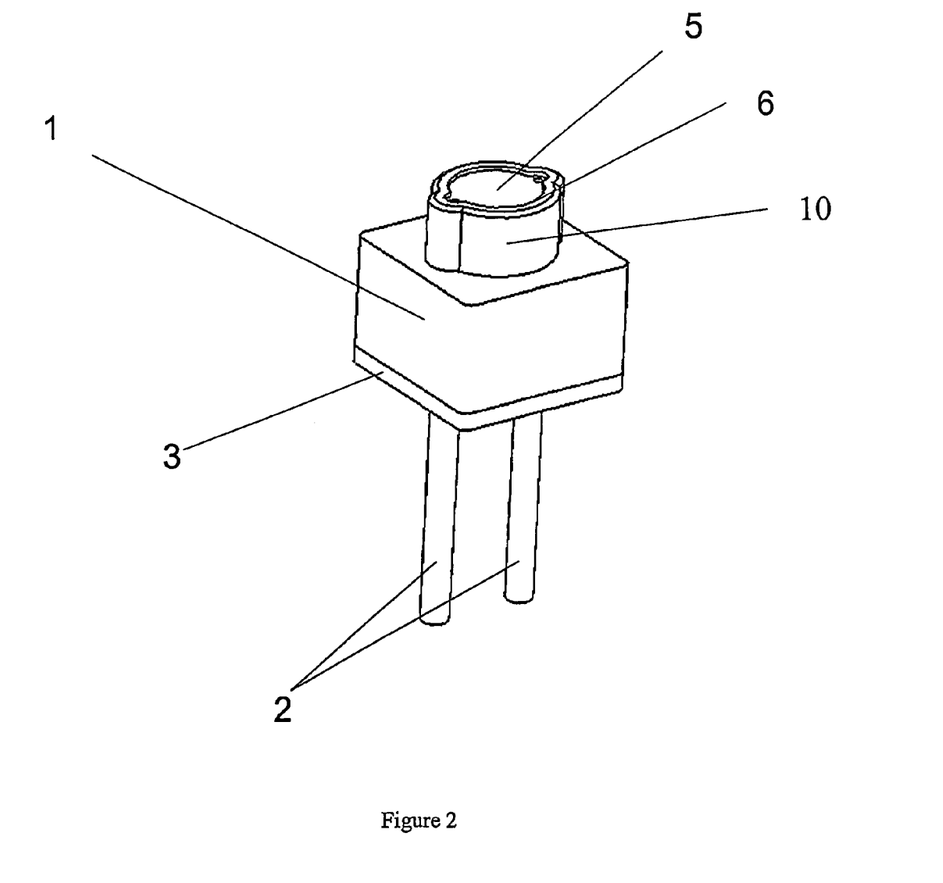
FIG. 2 shows a perspective view of part of the flow cell and counter electrode of FIG. 1.

FIGS. 1 and 2 show the arrangement of a flow cell which may be used with a chemical sensor. The arrangement comprises a flow cell element (1), fluid channels (2) and the counter electrode (3). The sensor element is intended to be exposed to the sample and the sensor surface will accordingly interact with components of the sample. The flow cell (9) includes a recess (5) and inlet and outlet fluid channels (4) for leading the sample fluid through the recess. The recess is provided within an abutting part (10) of the flow cell element and is surrounded by an abutment surface (6). When brought into sealing engagement, as shown in FIG. 1, the sensor surface and the abutment surface seal the recess, thus cooperatively forming a flow cell between the flow cell element and the sensor. The counter electrode (3) is located on the flow cell element at the opposite side to the recess (5). The flow cell element (1) should be formed from an electrically insulating material (e.g. a plastics material), whereas the counter electrode should be made of electrically conducting material, preferably a metal. In most cases, the sensor element is at least partially made of an electrically conducting material. The sensor may or may not be coated with an insulating material.

A voltage source (8) has output terminals connected respectively to the counter electrode and to the sensor as shown in FIG. 1. Accordingly, a corresponding potential will be applied between the counter electrode and sensor.

The present invention allows simplification of experimental procedures by enabling repeated use of the same buffer. Previously, immobilisation of compounds of different pI required the use of specially tuned buffers for each different compound. Using the present invention, the transport of compounds to the sensor surface can be modulated with the strength of the electric field and changes in buffer therefore become unnecessary.

Aside from control of the transport of charged molecules in the vicinity of the sensor surface, an applied electric field can also be used to control the binding orientation of the immobilised molecule. An electric field can be used to orient a relatively charged side of a molecule, e.g. a receptor, away from or towards the sensor surface.

Example 2

Figure 4:
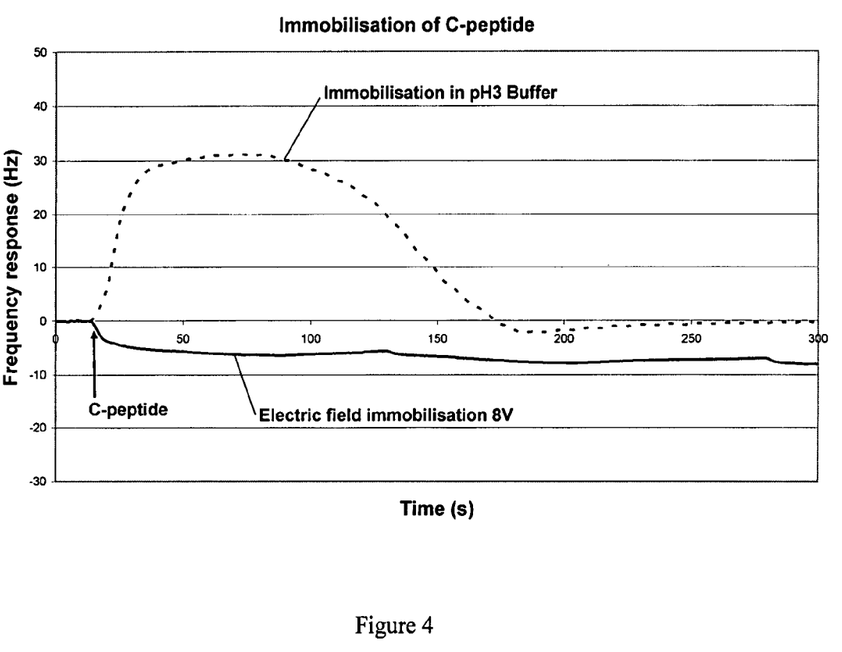
FIG. 4 shows the results of a QCM-based study of immobilisation of C-peptide to a carboxylated surface. The graph presents the immobilisation of C-peptide under the influence of an electric field and, for comparison, the unsuccessful immobilisation of C-peptide with the peptide dissolved in a pH 3 buffer and without the application of an electric field (dashed line)

Immobilisation of C-peptide onto a Carboxylated Sensor Surface with Amine Coupling In this study, an Attana 80° C. continuous flow biosensor was modified to allow for application of an electrical field over the QCM sensor surface and the flow cell. FIG. 2 shows schematically the Attana flow cell equipped with Cu-electrode (3) for application of an electric field over the QCM sensor surface. A gold surface modified with a self-assembled monolayer of a carboxyl-terminated n-alkylthiol (with an alkyl chain length of 15) was used as sensor surface. Since the C-peptide has a pI of below 3 and is negatively charged at a pH generally considered suitable for the coupling reaction (pH 4-8), it is difficult to achieve immobilisation onto the negatively charged carboxyl surface. By applying an electrical field, the effect of the repulsive electrostatic forces can be overcome and the C-peptide can react with the activated carboxylated surface via its N-terminus. In order to maximise the electrical field over the flow chamber and the sensor surface, MilliQ water was used as running buffer throughout the experiments. For activation of the carboxyl surface a mixture of EDC (0.2M) and NHS (0.05M) in water was allowed to flow over the surface for 16 minutes. The two components were mixed together immediately prior to injection, in order to maximise their activity. After activation of the surface, a negative potential of 4V was applied to the Cu-plate and the C-peptide was allowed to flow over the surface for 4 minutes. Next, the potential was set to zero and duplicate injections of ethanolamine (1M, pH 8.5) were carried out to deactivate the surface. In order to remove non-specifically bound material, 50 µl of Guanidine Hydrochloride (6M) was injected over the surface. The sequence of immobilisation is shown in FIG. 4 as a real-time measurement with an Attana QCM biosensor. Binding to the surface is represented by a decrease in frequency, whereas desorption from the surface is indicated by frequency increases. The binding of the peptide to the surface is demonstrated by the decrease in frequency following the duplicate injections of C-Peptide (20 µg/ml, 50 µl). The subsequent deactivation of the surface with duplicate ethanolamine injections resulted in a significant persistent decrease (due to binding of the deactivation agent to the surface). The regeneration agent, which was injected to remove non-covalently bound material, resulted in a reversible frequency decrease (due to changes in, for instance, ionic strength and pH; data not shown).

Figure 5:
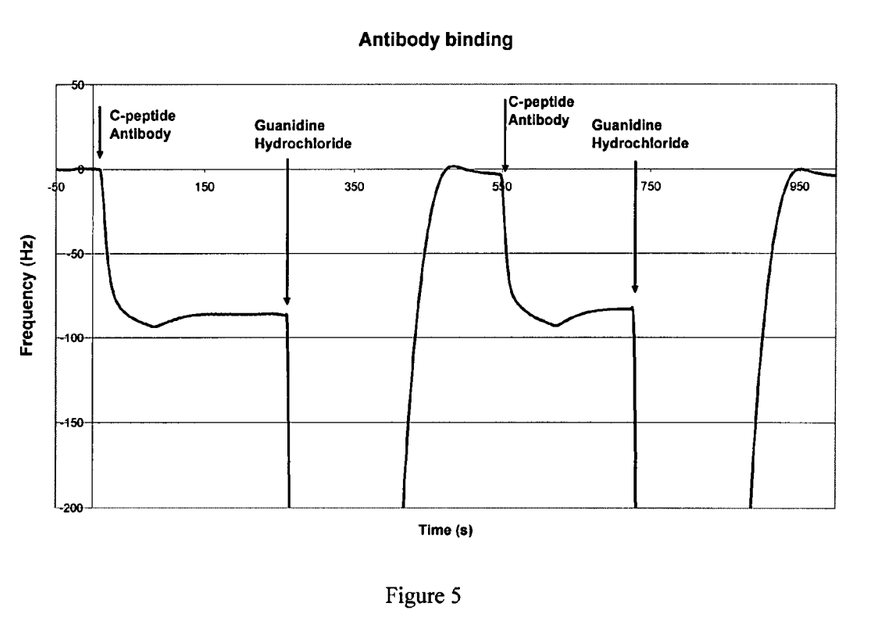
FIG. 5 shows the results of a QCM-based study of binding of an anti-C-peptide monoclonal antibody to the immobilised C-peptide obtained in FIG. 4.

Verification of peptide immobilisation was performed by injection of 50 µl of an anti-C-peptide monoclonal antibody (50 µg/ml). As shown in FIG. 5, the antibody binds extensively to the surface, first leading to a frequency shift of around 85 Hz and then, after regeneration (Guanidine HCl, 0.6M) with a shift of around 80 Hz. The fact that the peptide surface can be regenerated with a strong regeneration agent such as Guanidine Hydrochloride shows that the electric field-assisted immobilisation is indeed successful for binding the peptide covalently to the surface and that a very stable sensor surface is achieved.

In a reference experiment, immobilisation was performed without the use of an electric field but with the other experimental conditions as described above, except for the use of a buffer with pH 3 to reduce to a greater extent the negative charge on the C-peptide. Despite the use of more favourable buffer conditions, introduction of C-peptide to the surface without the electric field showed no stable binding—the reversible signal in the reference experiment (FIG. 4, dashed line) is due to viscosity and conductivity changes with the pH 3 buffer—nor did the C-peptide antibody show any binding to the resulting surface. A similar reference experiment using a buffer with pH 5 yielded essentially the same negative result as seen at pH 3.

The invention claimed is:

1. A method of covalently immobilising a charged chemical species, comprising providing a sensor surface for a chemical sensor, wherein the sensor surface bears a net negative charge and comprises functional groups capable of forming covalent bonds with the charged chemical species, applying an electric field between the charged chemical species and the sensor surface, wherein an electrostatic repulsion between the charged species and the sensor surface is reduced, and covalently immobilizing the charged chemical species on the sensor surface, wherein the sensor surface bears a plurality of carboxyl groups, and further wherein the charged chemical species is a polypeptide that has a net negative charge during the immobilisation.

2. The method according claim 1 wherein the net charge on the charged chemical species is pH-dependent.

3. The method according to claim 1 wherein the polypeptide has an isoelectric point of approximately 4 or less.

4. The method according to claim 1 wherein the surface contains functional groups at a reduced surface density, wherein the density of the functional groups are reduced by interspersion of the molecules bearing the functional groups among molecules bearing neutral and non-activated groups instead of functional groups.

5. The method according to claim 1 wherein the sensor surface comprises a tridimensional porous matrix, wherein the functional groups of the sensor surface are distributed in three dimensions within the porous matrix.

6. The method according to claim 1 wherein the electric field is applied by means of working and counter electrodes in electrical contact with a dispersion of the charged chemical species introduced into the vicinity of the sensor surface, wherein one of the working or counter electrodes is formed by a metallic component of the sensor surface.

7. The method according to claim 6 further comprising a reference electrode, wherein the reference electrode is directly or indirectly electrically connected to the dispersion and the working and counter electrodes.

8. The method according to claim 1 wherein the electric field is applied by means of working and counter electrodes, at least one of which is substantially electrically insulated from a dispersion of the charged chemical species introduced into the vicinity of the sensor surface.

9. The method according to claim 8 wherein at least one of the working or counter electrodes is formed by a metallic component of the sensor surface.

10. The method according to claim 9 wherein the metallic component of the sensor surface is in electrical contact with the dispersion of the charged chemical species.

11. The method according to claim 10 wherein the metallic component of the sensor surface is at least partially covered with a layer of low electrical conductivity material.

12. The method according to claim 11 wherein the low electrical conductivity material comprises a polymer or a self-assembled monolayer.

13. The method according to claim 8 wherein one or both of the working or counter electrodes is located adjacent the sensor surface and is substantially electrically insulated therefrom.

14. The method according to claim 13 wherein the sensor surface is formed from a material of low electrical conductivity.

15. The method according to claim 8, wherein both the working and counter electrodes are substantially electrically insulated from the dispersion of the charged chemical species.

16. The method according to claim 1 wherein the chemical sensor resides within, or forms part of, a flow cell for ingress and egress of the charged chemical species to and from the vicinity of the sensor surface.

17. The method according to claim 1 wherein the chemical sensor is a chemical sensor selected from the group consisting of a piezoelectric sensor, an evanescent wave chemical sensor, an ellipsometry sensor, and an optical waveguide chemical sensor.

18. The method according to claim 1 further comprising reversing the applied electric field.

19. The method of claim 1, wherein the chemical sensor is mass sensitive and wherein the covalent immobilization of the charged chemical species to the sensor surface is measured by applying the electric field to control binding orientation of the charged chemical species to the sensor surface.

20. The method of claim 1, wherein:
(a) the sensor surface is a metallic surface in electrical connectivity with a power source to form an electrode; and
(b) the functional groups are distributed in three dimensions within porous matrix; and wherein the method further comprises loading the charged chemical species to bind to the functional groups by adding a dispersion of the charged chemical species and applying the electric field with the metallic surface and a reference electrode.

21. The method of claim 20 wherein the metallic surface is composed of a noble metal film of either Ag or Au or an alloy thereof.

22. A chemical sensor comprising a sensor surface, wherein the sensor surface is obtained by the method of:
(a) providing a sensor surface for a chemical sensor, wherein the sensor surface comprises functional groups capable of forming covalent bonds with charged chemical species, and
(b) applying an electric field between the charged chemical species and the sensor surface, wherein an electrostatic repulsion between the charged species and the sensor surface is reduced, and covalently immobilizing the charged chemical species on the sensor surface, wherein the sensor surface bears a net negative charge, wherein the sensor surface bears a plurality of carboxyl groups, and further wherein the charged chemical species is a polypeptide that has a net negative charge during the immobilisation.

23. A mass-sensitive chemical sensor apparatus comprising a flow cell element, a sensor surface bearing a net negative charge and comprising functional groups capable of forming covalent bonds with charged chemical species, a dispersion of charged chemical species, and a voltage source for applying an electric field between the charged chemical species and the sensor surface so as to reduce the electrostatic repulsion therebetween for covalent immobilization of the charged chemical species on the sensor surface, wherein the sensor surface a plurality of carboxyl groups, and further wherein the charged chemical species is a polypeptide that has a net negative charge during the immobilisation.

24. The mass-sensitive chemical sensor apparatus according to claim 23 wherein the flow cell element is for ingress and egress of the dispersion of the charged chemical species to and from the vicinity of the sensor surface, wherein the chemical sensor resides within, or forms part of, the flow cell.

25. The mass-sensitive chemical sensor apparatus according to claim 23 wherein the means for applying an electric field comprises working and counter electrodes, at least one of which does not, in use, come into physical contact with a dispersion of the charged chemical species introduced into the vicinity of the sensor surface.

26. The mass-sensitive chemical sensor apparatus of claim 23 wherein the apparatus further comprises a detection device selected from the group consisting of an evanescent wave device, a surface plasmon resonance sensor, a piezoelectric device, and a quartz crystal microbalance.

27. The mass-sensitive chemical sensor apparatus of claim 23, wherein:
(a) the sensor surface is a metallic surface in electrical connectivity with a power source for applying the electric field;
(b) the functional groups are distributed in three dimensions within and throughout a porous matrix; and
(c) the charged chemical species is bound to the functional groups within the porous matrix.

28. The sensing surface of claim 27 further comprising a detecting device in contact with the metallic surface, wherein the detecting device is an evanescent wave device, a surface plasmon resonance sensor a piezoelectric device a quartz crystal microbalance.

* * * * *